(12) United States Patent
Harada et al.

(10) Patent No.: US 9,107,876 B2
(45) Date of Patent: Aug. 18, 2015

(54) SURFACE ANESTHETIC AGENT

(75) Inventors: Koji Harada, Yamaguchi (JP);
Yasutaka Itashiki, Yamaguchi (JP);
Toyoko Harada, Yamaguchi (JP);
Yoshiya Ueyama, Yamaguchi (JP)

(73) Assignee: YAMAGUCHI UNIVERSITY, Yamaguchi (JP)

( * ) Notice: Subject to any disclaimer, the term of this patent is extended or adjusted under 35 U.S.C. 154(b) by 522 days.

(21) Appl. No.: 13/379,107

(22) PCT Filed: Jun. 30, 2010

(86) PCT No.: PCT/JP2010/004312
§ 371 (c)(1),
(2), (4) Date: Dec. 19, 2011

(87) PCT Pub. No.: WO2011/001676
PCT Pub. Date: Jan. 6, 2011

(65) Prior Publication Data
US 2012/0101158 A1    Apr. 26, 2012

(30) Foreign Application Priority Data

Jul. 2, 2009 (JP) ................. 2009-157425

(51) Int. Cl.
*A61K 31/136* (2006.01)
*A61K 31/245* (2006.01)
*A61K 31/167* (2006.01)
*A61K 31/137* (2006.01)

(52) U.S. Cl.
CPC ............. *A61K 31/137* (2013.01); *A61K 31/167* (2013.01); *A61K 31/245* (2013.01)

(58) Field of Classification Search
CPC . A61K 31/136; A61K 31/245; A61K 31/167; A61K 31/137
USPC ................................ 514/537, 563
See application file for complete search history.

(56) References Cited

U.S. PATENT DOCUMENTS 5,885,597 A    3/1999    Botknecht et al.

FOREIGN PATENT DOCUMENTS

| JP | 09-077662 | 3/1997 |
|---|---|---|
| JP | 10-306040 | 11/1998 |
| JP | 2002-275093 | 9/2002 |
| JP | 2003-512401 | 4/2003 |
| JP | 2003-532678 | 11/2003 |
| JP | 2006-527734 | 12/2006 |
| JP | 2007-262030 | 10/2007 |
| JP | 4060884 | 12/2007 |
| JP | 2008-029681 | 2/2008 |
| JP | 2009-506076 | 2/2009 |
| WO | WO 2006/065870 | 6/2006 |
| WO | WO 2007/055279 A1 | 5/2007 |
| WO | WO 2007/103555 | 9/2007 |
| WO | WO 2008/036912 | 3/2008 |

OTHER PUBLICATIONS

Rosivack et al., "An Analysis of the Effectiveness of Two Topical Anesthetics," Anesthesia Progress, vol. 37, No. 6, pp. 290-292, Nov. 1990.
European Search Report for European Application No. 10793849.0, Yamaguchi University, Nov. 28, 2012, 6 pages.
Mrose, "Local Anesthetics: Do Benzocaine and Lidocaine Act at the Same Single State?," J. Gen. Physiol., vol. 71, No. 2, pp. 223-225, Feb. 1978.
Schmidtmayer et al., "Interaction of Lidocaine and Benzocaine in Blocking Sodium Channels," Pflügers Arch., vol. 387, No. 1, pp. 47-54, Aug. 1980.

*Primary Examiner* — Sreeni Padmanabhan
*Assistant Examiner* — Sahar Javanmard
(74) *Attorney, Agent, or Firm* — Kenneth H. Sonnenfeld; Margaret B. Brivanlou; King & Spalding LLP

(57) ABSTRACT

Provided is an anesthetic agent which can exhibit an anesthetic effect rapidly when adhered on mucosal membranes, the skin or the like by means of application or the like in local anesthesia, particularly surface anesthesia. Prepared are: a fast-acting surface anesthetic agent containing lidocaine and ethyl paraaminobenzoate at a specific ratio; and a super fast-acting surface anesthetic agent containing lidocaine, ethyl paraaminobenzoate and adrenaline at a specific ratio.

4 Claims, 4 Drawing Sheets

Mixing ratio of Lidocaine and Ethyl Paraaminobenzoate

SURFACE ANESTHETIC AGENT

TECHNICAL FIELD

The present invention relates to a surface anesthetic agent containing lidocaine and ethyl paraaminobenzoate, preferably lidocaine, ethyl paraaminobenzoate and adrenaline as active ingredients, which exhibits anesthetic effects within 3 minutes after being applied or sprayed.

BACKGROUND ART

Conventionally, as a local anesthesia, surface anesthesia, infiltration anesthesia, conduction anesthesia and the like are known. Among them, the surface anesthesia is an anesthesia in which an anesthetic agent is applied or sprayed onto the mucosal membrane or skin whereby to be adhered or infiltrated, which is conducted in order to alleviate the pain of an injection needle in the following infiltration anesthesia or conduction anesthesia by injection, and is mainly applied for dental treatment of children and the like.

The infiltration anesthesia is a method that anesthetizes an infiltrated part by injection, which is a partial anesthesia, and is used when dental extraction or tooth drilling is conducted in dentistry, or when simple incision operation is conducted in surgery, and the like.

In addition, the conduction anesthesia is a method that anesthetizes even to the tip part on which the nerve runs by injecting an anesthetic agent in the vicinity of the nerve. In dentistry, the conduction anesthesia is a method that anesthetizes from back teeth to anterior teeth on the to-be-anesthetized side by injecting an anesthetic agent mainly around the nerve that enters the bone of the mandible.

A local anesthetic drug is generally classified into an ester type, an amide type or anilide type. Examples of the ester type include benzoate esters such as cocaine, tropacocaine, procaine, tetracaine, piperocaine and stovaine, alkoxybenzoate esters such as cyclomethycaine and parethoxycaine, aminobenzoate esters such as methyl paraaminobenzoate and ethyl paraaminobenzoate. In addition, as the amide or anilide type, lidocaine (Xylocaine) and the like are known.

These anesthetic drugs are constituted as a local anesthetic agent by further blending a vasoconstrictive drug such as catecholamines including epinephrine (adrenaline) and norepinephrine for the purpose of sustaining the effects; a preservative stabilizer such as an antioxidant, e.g., butylhydroxytoluene, gallic acid esters, and the like and a stabilizer agent, e.g., gelatin, agar, starch, thiourea, citric acid, L-methionine, glutamic acid, fructose, sucrose, lactose, thioglycerin, and the like; or, a sweetener, a thickening agent and the like particularly for an oral surface anesthetic agent and the like.

As an improvement in the surface anesthetic agent, a conventional method of enhancing the persistence (for example, Patent Documents 1, 2 and 5), a method of rapidly releasing an anesthetic after operation (for example, Patent Document 3), a method of improving preservative stability of an anesthetic agent (for example, Patent Documents 4 and 5) and the like are proposed. In addition, as an improvement in the fast-acting property of a surface anesthetic agent, a fast-acting percutaneous anesthetic drug in which lidocaine, prilocaine and tetracaine are mixed (for example, Patent Document 6) is proposed. However, in Examples of Patent Document 6, only about 55.7% of the people had pain "0" after 30 minutes of the application.

In addition, proposed are a skin-external agent having an action of ameliorating itching, which is a mixture of a local anesthetic agent, urea, a refreshing agent, alcohol and water (for example, Patent Document 7) and a method of suppressing or ameliorating pain from an surgically closed wound area, which applies a local anesthetic agent onto the outer surface of a wound area (for example, Patent Document 8). However, these documents do not disclose that a fast action property has been improved in a local anesthetic agent to be used.

PRIOR ART DOCUMENTS

Patent Documents

Patent Document 1: Japanese Patent No. 4060884
Patent Document 2: Japanese Unexamined Patent Application Publication No. 2002-275093
Patent Document 3: Japanese Unexamined Patent Application Publication (Translation of PCT Application) No. 2003-532678
Patent Document 4: Japanese Unexamined Patent Application Publication No. 9-77662
Patent Document 5: Japanese Unexamined Patent Application Publication No. 10-306040
Patent Document 6: Japanese Unexamined Patent Application Publication (Translation of PCT Application) No. 2006-527734
Patent Document 7: Unexamined. Patent Application Publication No. 2007-262030
Patent Document 8: Japanese Unexamined Patent Application Publication (Translation of PCT Application) No. 2003-512401

SUMMARY OF INVENTION

Object to be Solved by the Invention

The surface anesthesia is a preliminary treatment mainly to avoid the pain of an injection needle in a subsequent actual anesthetic given by an injection and the like, and generally does not need to be sustained for a long time, but an important thing is that effects can be obtained immediately after the treatment. For example, when a dental operation such as dental extraction is conducted, first, a surface anesthetic agent is given, and upon confirming that the anesthetic has worked, an infiltration anesthesia is conducted. A generally marketed surface anesthetic agent requires from 3 to 5 minutes for exhibiting the effects after conducting surface anesthesia. In the meantime, an operator has to only wait without doing anything. Further, it cannot be said that this waiting time is good for the patient, and the waiting time is a waste of time. Generally, when a person has to wait for a next treatment to be conducted, the person will not feel any algesia and can wait if the waiting time is within 3 minutes, but will be anxious if the waiting time is beyond 3 minutes. Thus, some operators moved to a next treatment such as injection before surface anesthesia exhibits the effects sufficiently, and thus often gave patients the pain. An object of the present invention is to provide a fast-acting surface anesthetic agent that gives effects more rapidly after being applied or sprayed.

MEANS TO SOLVE THE OBJECT

The present inventors investigated earnestly to solve the object mentioned above, and first focused on lidocaine [2-(diethylamino)-N-(2,6-dimethylphenyl) acetamide], and investigated the combination use with adrenaline which is a vasoconstrictive drug. When lidocaine and adrenaline are used in combination, the fast-acting of the surface anesthetic action gradually increases as the addition amount of adrenaline increases. However, when adrenaline is used in a large amount, adverse effects might occur, which is not preferable. Next, the combination use of adrenaline with ethyl paraaminobenzoate instead of lidocaine was investigated, and the fast-acting property of the surface anesthetic action was never recognized even though the addition amount of adrenaline increased. Therefore, just in case, the present inventors investigated the combination use of adrenaline with a mixture of lidocaine and ethyl paraaminobenzoate, and unexpectedly found that the fast-acting property of the surface anesthetic action was markedly improved. To elucidate the cause thereof, the present inventors used a combination of lidocaine and ethyl paraaminobenzoate, and found that the fast-acting property of the surface anesthetic action was synergistically improved at a certain blending ratio. Then, using the tetracaine [4-(butylamino)benzoate 2-(dimethylamino)ethyl] that belongs to the benzoate esters to which ethyl paraaminobenzoate also belongs, the combination use of lidocaine with tetracaine, or the combination use of lidocaine, tetracaine and adrenaline was investigated similarly, but the fast-acting property of the surface anesthetic action was not synergistically improved. The present inventors completed the present invention based on these findings.

Specifically, the present invention relates to (1) a surface anesthetic agent, containing lidocaine and ethyl paraaminobenzoate in a mass ratio of 1:99 to 47:53; (2) the surface anesthetic agent according to "1", wherein lidocaine and ethyl paraaminobenzoate are contained in a mass ratio of 6:94 to 18:82; (3) the surface anesthetic agent according to "1" or "2", wherein adrenaline is further contained in addition to lidocaine and ethyl paraaminobenzoate; and (4) the surface anesthetic agent according to any one of "1" to "3", wherein adrenaline is contained in an amount of 0.1 to 0.001 part by mass with respect to total 100 parts by mass of lidocaine and ethyl paraaminobenzoate.

In addition, the present invention relates to (5) a method of using a composition containing lidocaine and ethyl paraaminobenzoate in a mass ratio of 1:99 to 47:53, for production of a surface anesthetic agent; (6) the method according to "5", wherein the composition contains lidocaine and ethyl paraaminobenzoate in a mass ratio of 6:94 to 18:82; (7) the method according to "5" or "6", wherein the composition further contains adrenaline in addition to lidocaine and ethyl paraaminobenzoate; and (8) the method according to any one of "5" to "7", wherein the composition contains 0.1 to 0.001 part by mass of adrenaline with respect to total 100 parts by mass of lidocaine and ethyl paraaminobenzoate.

Furthermore, as an embodiment, the present invention relates to (9) a method of using a composition containing lidocaine and ethyl paraaminobenzoate in a mass ratio of 1:99 to 47:53 as a surface anesthetic agent; (10) the method according to "9", wherein the composition contains lidocaine and ethyl paraaminobenzoate in a mass ratio of 6:94 to 18:82; (11) the method according to "9" or "10", wherein the composition further contains adrenaline in addition to lidocaine and ethyl paraaminobenzoate; and (12) the method according to any one of "9" to "11", wherein the composition contains 0.1 to 0.001 part by mass of adrenaline with respect to total 100 parts by mass of lidocaine and ethyl paraaminobenzoate.

EFFECT OF THE INVENTION

According to the present invention, it is possible to provide a fast-acting surface anesthetic agent that exhibits anesthetic effects remarkably within 3 minutes, particularly 1 to 2 minutes, particularly after being applied or sprayed onto the mucosal membrane or gum of the mouth, and that causes no pain by the subsequent injection. The surface anesthetic agent of the present invention is also effective with respect to the skin, but in this case, the effects may exhibit more slowly than that to the mucosal membrane, and it may require 5 to 6 minutes.

BRIEF DESCRIPTION OF DRAWINGS

In FIG. 1, the vertical axis represents the pain degree when an injection needle is stabbed, wherein "5" represents no anesthetic, and reversely "0" represents no feeling of pain. In addition, the horizontal axis represents time (minute).

In FIG. 2, the vertical axis represents time (minute) to no feeling of pain of an injection needle after the application prior to an anesthesis, and the horizontal axis represents the blending ratio of lidocaine and ethyl paraaminobenzoate (mass ratio).

In FIG. 4, the vertical axis represents the pain degree when an injection needle is stabbed, wherein "5" represents no anesthetic, and reversely "0" represents no feeling of pain. The horizontal axis represents time (minute).

MODE OF CARRYING OUT THE INVENTION

Figure 1:
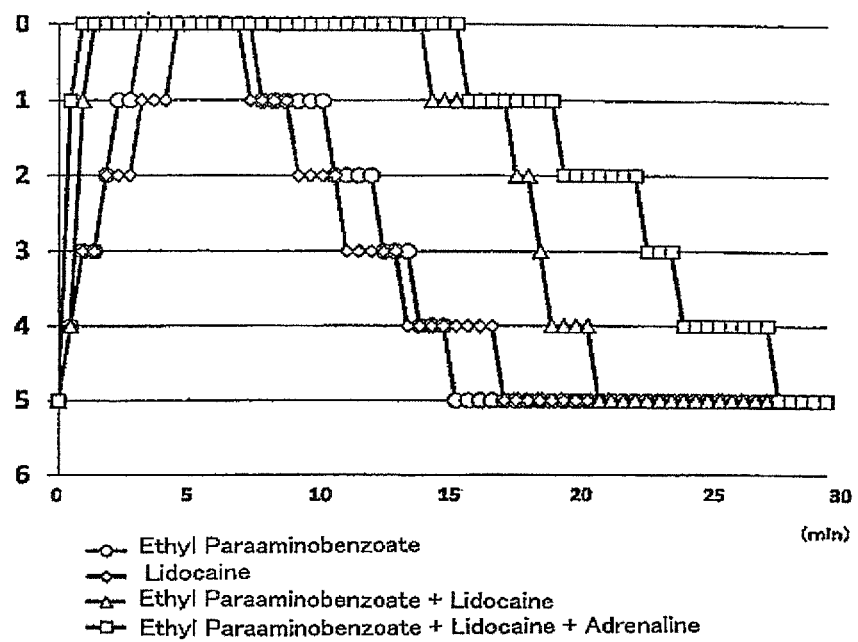
[FIG. 1] It is a graph that shows comparison of the expression time and the duration of anesthetic effects by the combination use of lidocaine and ethyl paraaminobenzoate of the present invention, the combination use of lidocaine, ethyl paraaminobenzoate and adrenaline, and conventionally used ethyl paraaminobenzoate alone and lidocaine alone.

The surface anesthetic agent of the present invention is not particularly limited as long as it is an anesthetic agent containing lidocaine and ethyl paraaminobenzoate in a mass ratio of 1:99 to 47:53, for example, an anesthetic agent containing lidocaine and ethyl paraaminobenzoate in a blending ratio of 8:92 to 90:10 when lidocaine at a concentration of 2% by mass and ethyl paraaminobenzoate at a concentration of 20% by mass are used. In addition, the use method of the present invention is not particularly limited as long as it is a method of using a composition containing lidocaine and ethyl paraaminobenzoate in a mass ratio of 1:99 to 47:53, for example, a composition containing lidocaine and ethyl paraaminobenzoate in a blending ratio of 8:92 to 90:10 when lidocaine at a concentration of 2% by mass and ethyl paraaminobenzoate at a concentration of 20% by mass are used for the production of a surface anesthetic agent. The lidocaine and the ethyl paraaminobenzoate mentioned above are known as local anesthetic drugs, and commercially available lidocaine and ethyl paraaminobenzoate may be advantageously used.

The mass ratio of lidocaine and ethyl paraaminobenzoate in the surface anesthetic agent of the present invention or the use method of the present invention mentioned above is preferably in a ratio of 3:97 to 31:69 from the viewpoint of the fast-acting property of the surface anesthetic action. For example, when lidocaine at a concentration of 2% by mass and ethyl paraaminobenzoate at a concentration of 20% by mass are used, the blending ratio is 25:75 to 82:18. Particularly, the mass ratio of lidocaine and ethyl paraaminobenzoate is more preferably in a ratio of 6:94 to 18:82 from the viewpoint of the fast-acting property of the surface anesthetic action. For example, when lidocaine at a concentration of 2% by mass and ethyl paraaminobenzoate at a concentration of 20% by mass are used, the blending ratio is 40:60 to 70:30.

The lidocaine mentioned above is a white to light yellow crystal or crystalline powders, known as an anti-arrhythmic agent besides being a local anesthetic drug, also effective for symptoms such as neuralgia and numbness in a limb, sold from AstraZeneca under the product name of "XYLOCAINE", and also called "Lidoca." or "Kishiro" by medical experts. The "lidocaine" or "Xylocaine" in the present specification also includes lidocaine salts such as hydrochloric acid salt of lidocaine. In addition, ethyl paraaminobenzoate is a white crystal or crystalline powders, used as a local anesthetic drug as a medical product, and as a cosmetic product, it is used in a sun-block cream, foundation, lip stick, cream, emulsion and the like because of its strong action of absorbing ultraviolet rays.

To further enhance the fast-acting action of the surface anesthetic agent of the present invention, a small amount of adrenaline [(R)-4-(1-hydroxy-2-(methylamino)ethyl)benzene-1,2-diol], for example, about 0.0001 to 1 part by mass, preferably 0.001 to 0.1 part by mass, more preferably 0.003 to 0.03 part by mass of the adrenaline [(R)-4-(1-hydroxy-2-(methylamino)ethyl)benzene-1,2-diol] with respect to total 100 parts by mass of lidocaine and ethyl paraaminobenzoate may be added.

Adrenaline is known as a substance having a vasoconstriction action, and generally used for maintaining the persistence of local anesthetic effects. However, in the present invention, adrenaline is used as a substance remarkably accelerating the effects as a surface anesthetic agent. However, the persistence of effects also increases naturally.

Since adrenaline has actions of raising heart rate and blood pressure, opening pupils, raising blood glucose level, and the like, adrenaline possibly may have a bad influence particularly on the elders, children or persons having a cardiac disease or diabetes, and thus is desired to be used in a small amount as possible as described above.

The surface anesthetic agent of the present invention is an anesthetic agent that exhibits anesthetic effects rapidly after being applied, preferably a local anesthetic agent that exhibits a painless effect within 3 minutes, further preferably within 2.5 minutes, particularly preferably within 2 minutes, still particularly preferably within 1 minute.

To the surface anesthetic agent of the present invention, conventionally known additives in a local anesthetic agent, for example, a preservative stabilizer agent (an antioxidant such as butylhydroxytoluene and gallic acid esters, a stabilizer such as gelatin, agar, starch, thiourea, citric acid, L-methionine, glutamic acid, fructose, sucrose, lactose and thioglycerin), a thickening agent, a flavoring agent, a sweetener, a diluting agent, a solvent and the like may further be blended.

Examples of the dosage form of the surface anesthetic agent of the present invention include a liquid form, a jelly form, an ointment form, a seal (PENLES) form and the like. Examples of the use form include application, adherence, spray, attachment and the like. As the ingredient of the anesthetic drug, the active ingredient is generally used conveniently as diluted to about 0.1 to 50% by mass, preferably 1 to 25% by mass with a solvent or other additives. In addition, the application amount may be similar to the application amount of a conventional surface anesthetic agent.

The surface anesthetic agent of the present invention is used similarly to conventionally known surface anesthetic agents. Specifically, the surface anesthetic agent of the present invention is applied to whole mammals, particularly adhered or infiltrated onto the mucosal membrane or the skin to perform anesthesia. The surface anesthetic agent of the present invention is generally used to alleviate the stabbing pain of an injection needle to be received later, prior to infiltration anesthesia or conduction anesthesia by injection when an operation and the like are conducted. Of course, the surface anesthetic agent of the present invention may also be used for the purpose of alleviating a pain such as stomatitis, tooth pain and neuralgia, for the purpose of alleviating a pain when a needle is inserted in conducting infusion, for the purpose of alleviating a pain when an endoscope, a large intestine fiber or a pernasal tube is used.

Hereinafter, the present invention will be specifically explained with Examples. However, the technical scope of the present invention is not limited to these Examples. In Examples, used were ethyl paraaminobenzoate ("Hurricaine Gel (trademark)" manufactured by Daito Pharmaceutical Co., Ltd.: 20% by mass concentration), lidocaine ("Xylocaine jelly (trademark)" manufactured by AstraZeneca: 2% by mass concentration), tetracaine ("COPALON (trademark)" manufactured by SHOWA YAKUHIN KAKO CO., LTD.: 6% by mass solution) and adrenaline ("BOSMIN SOLUTION (trademark)" manufactured by DAIICHI SANKYO COMPANY, LIMITED: 0.1% by mass concentration).

EXAMPLE 1

(1) As a sample of ethyl paraaminobenzoate alone (Comparative Example 1-1), 200 mg Hurricaine Gel (40 mg ethyl paraaminobenzoate) was attached to a cotton swab, and applied to the buccal mucosal membrane.

(2) As a sample of lidocaine alone (Comparative Example 1-2), 200 mg Xylocaine jelly (4 mg lidocaine) was attached to a cotton swab, and applied to the buccal mucosal membrane.

(3) As a sample of a combination use of ethyl paraaminobenzoate and lidocaine (Example 1-1), 200 mg of a mixture of Hurricaine Gel and Xylocaine jelly in an equal amount (20 mg ethyl paraaminobenzoate and 2 mg lidocaine) was attached to a cotton swab, and applied to the buccal mucosal membrane.

(4) As a sample of a triple combination use of ethyl paraaminobenzoate, lidocaine and adrenaline (Example 1-2), 200 mg of a mixture of Hurricaine Gel and Xylocaine jelly in an equal amount (20 mg ethyl paraaminobenzoate and 2 mg lidocaine) and 10 mg adrenaline liquid (0.01 mg adrenaline) was attached to a cotton swab, and applied to the buccal mucosal membrane.

Various surface anesthetic agents mentioned above were applied to the buccal mucosal membrane, and then a needle was stabbed, and the time for the painless effect to be exerted and the time for the pain to start again were measured. The results thereof are shown in FIG. 1. When ethyl paraaminobenzoate and lidocaine were used in combination (Example 1-1), anesthetic painless effects were obtained 1 minute 30 seconds after the application. In addition, when a combination of ethyl paraaminobenzoate and lidocaine with adrenaline were used (Example 1-2), anesthetic effect superior in fast-acting property was obtained where it became painless 1 minute after the application. On the other hand, when ethyl paraaminobenzoate alone was used (Comparative Example 1-1; -○-), 3 minutes and 30 seconds was required for the painless effect to be exerted after the application, and when lidocaine alone was used (Comparative Example 1-2; -◇-), 5 minutes was required for the painless effect to be exerted after the application, respectively. From these results, it was found that when ethyl paraaminobenzoate and lidocaine were used in combination (Example 1-1; -△-), particularly when a combination of ethyl paraaminobenzoate and lidocaine with adrenaline was used (Example 1-2; -□-), the fast-acting property of the surface anesthetic action was synergistically improved.

EXAMPLE 2

Next, the relation of the blending ratio of lidocaine and ethyl paraaminobenzoate with the fast-acting property of the surface anesthetic action was studied. By varying the blending ratio of Xylocaine jelly and Hurricaine Gel, various surface anesthetic agents of lidocaine and ethyl paraaminobenzoate in mass ratios of 0:100 to 100:0 were prepared. For example, various surface anesthetic agents of lidocaine and ethyl paraaminobenzoate in mass ratios of 0:100, 1:99, 3:97, 6:94, 19:81, 31:69, 47:53, 80:20 and 100:0, were prepared by blending Xylocaine jelly and Hurricaine Gel in ratios of 0:200, 16:184, 50:150, 80:120, 140:60, 164:36, 180:20, 195:5 and 200:0, respectively. 200 mg of each of the prepared surface anesthetic agents, was applied to the buccal mucosal membrane similarly to Example 1, and then a needle was stabbed, and the time for the painless effect to be exerted was measured. The relation of the time for the painless effect to be exerted and the mass ratio of lidocaine and ethyl paraaminobenzoate is shown in FIG. 2.

Figure 2:
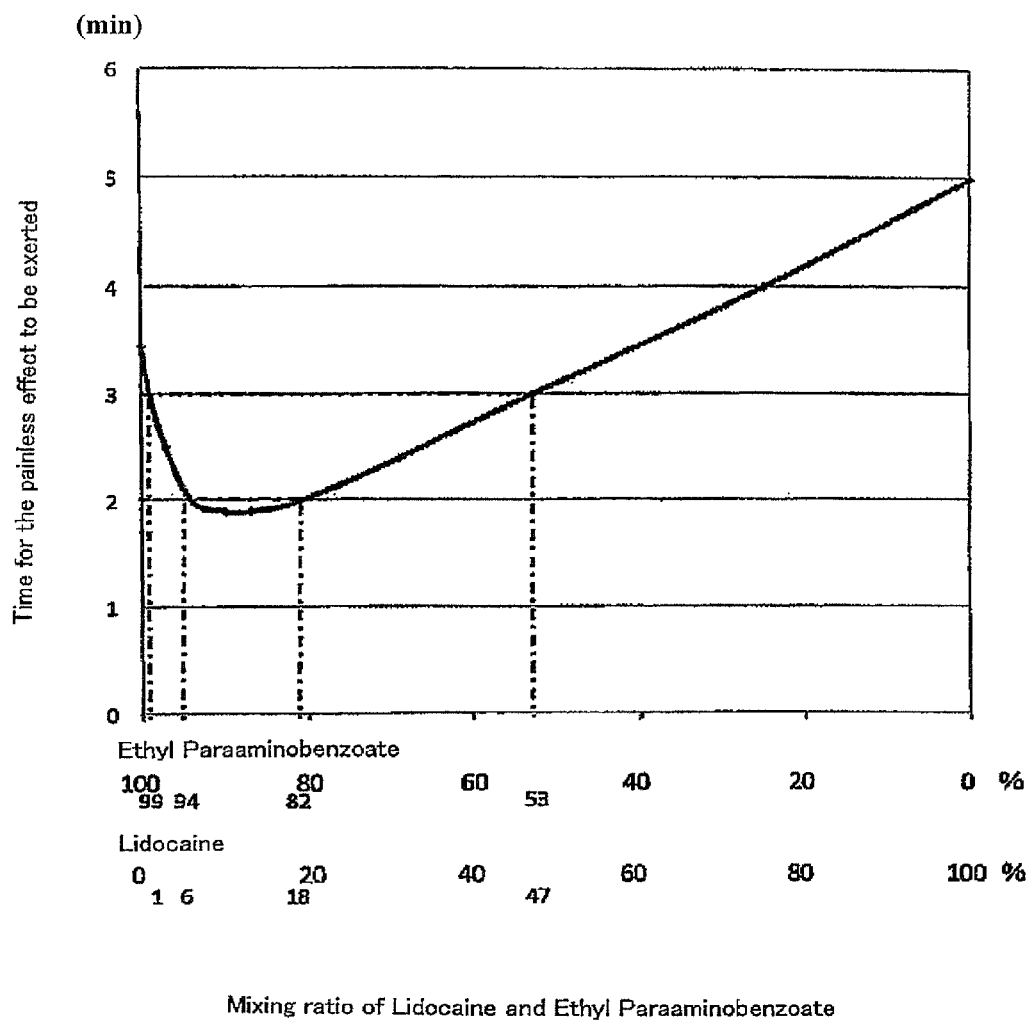
[FIG. 2] It is a graph that represents the relation of the blending ratio of lidocaine and ethyl paraaminobenzoate with the expression time of anesthetic effects in the present invention.

From FIG. 2, it is found that the time for the painless effect to be exerted after the application is within 3 minutes in a range of 1:99 to 47:53 mass ratio of lidocaine:ethyl paraaminobenzoate, whereas the time for the painless effect to be exerted is 5 minutes with lidocaine alone, and 3 minutes and 30 seconds with ethyl paraaminobenzoate alone. Particularly, it is found that the time for the painless effect to be exerted is about 2 minutes in a range of 6:94 to 18:82 ratio (mass ratio) mentioned above.

EXAMPLE 3

Figure 3:
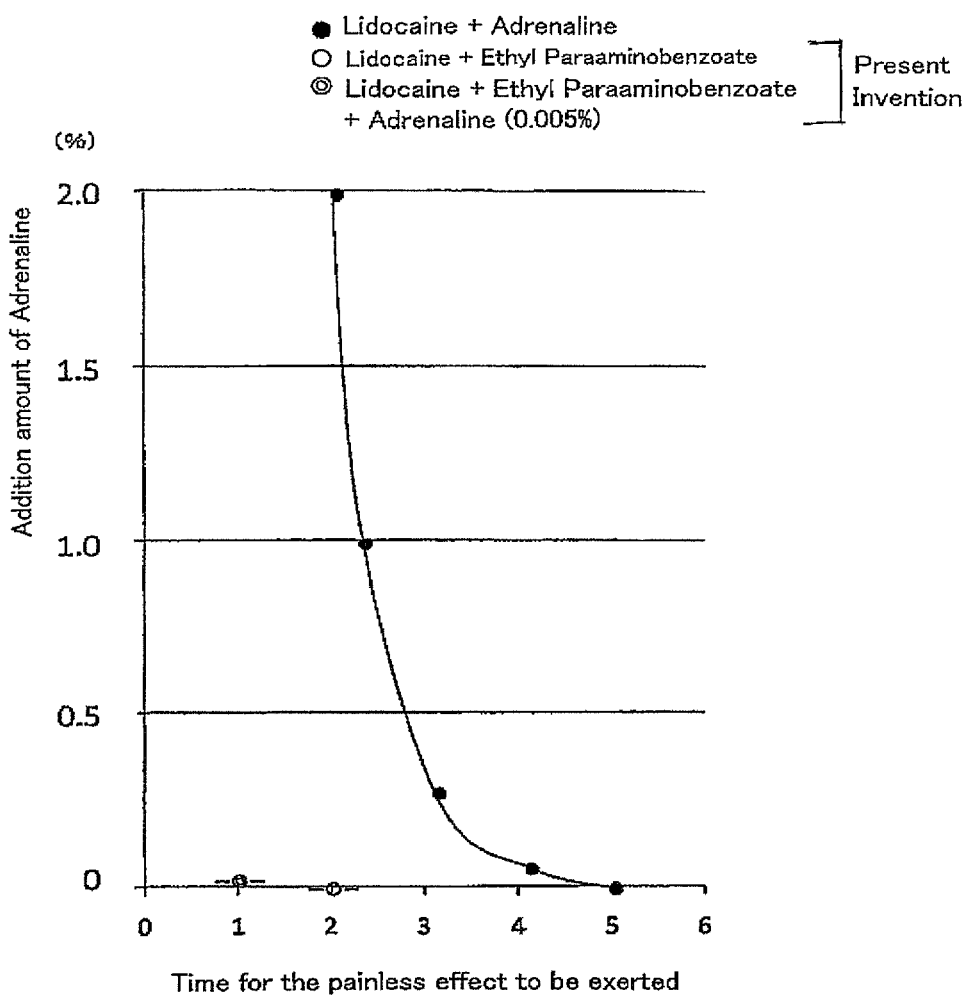
[FIG. 3] It is a graph that represents effects of adrenaline in the anesthetic agent of the present invention and an existing anesthetic agent on the time to no feeling of pain of an injection needle after the application.

To 4 mg lidocaine (Xylocaine jelly used in Example 1), 0 mg (0% by mass), 0.002 mg (0.05% by mass), 0.01 mg (0.25% by mass), 0.04 mg (1.0% by mass), and 0.08 mg (2.0% by mass) of adrenaline were added respectively, and the time until the surface anesthesia started to work was measured in each case. The application method and the measurement method for the results were carried out similar to those in Example 1. The results are shown in FIG. 3. In FIG. 3, besides lidocaine+adrenaline (-●-), the values of 20 mg ethyl paraaminobenzoate+2 mg lidocaine (-○-) and 20 mg ethyl paraaminobenzoate+2 mg lidocaine+adrenaline (0.005%) (-⊙-), which were the data when the surface anesthesia began to take effect in Example 1, were also shown. From FIG. 3, when adrenaline was added to lidocaine, as the addition amount of adrenaline increased, fast-acting property of the anesthetic increased. However, when adrenaline was used in a large amount, adverse effects may occur, and thus was not preferable. In addition, experiments were similarly carried out in which 0.002 mg (0.005% by mass), 0.01 mg (0.025% by mass). 0.04 mg (0.1% by mass), and 0.08 mg (0.2% by mass) of adrenaline were added respectively to 40 mg of ethyl paraaminobenzoate (Hurricaine Gel used in Example 1). However, effects of improving the fast-acting property by adrenaline were not observed (not shown in the figure). As described above, it is understood that effects of the present invention are superior.

Comparative Example 4

(1) As a sample of tetracaine alone, 200 mg (12 mg tetracaine) COPALON was attached to a cotton swab, and applied to the buccal mucosal membrane.

(2) As a sample of lidocaine alone, 200 mg Xylocaine jelly (4 mg lidocaine) was attached to a cotton swab, and applied to the buccal mucosal membrane.

(3) As a sample of a combination use of tetracaine and lidocaine, various mixtures of tetracaine and lidocaine in 92:8, 82:18, 67:33 and 43:57 mass ratios were prepared by varying the blending ratio of COPALON and Xylocaine jelly to 80:20, 60:40, 40:60 and 20:80. 200 mg of each of the prepared mixtures was attached to a cotton swab, and applied to the buccal mucosal membrane.

(4) As a sample of a triple combination use of tetracaine, lidocaine and adrenaline, a 200 mg mixture of COPALON and Xylocaine jelly in an equal amount (6 mg tetracaine and 2 mg lidocaine) and 10 mg adrenaline liquid (0.01 mg adrenaline) was attached to a cotton swab, and applied to the buccal mucosal membrane.

Figure 4:
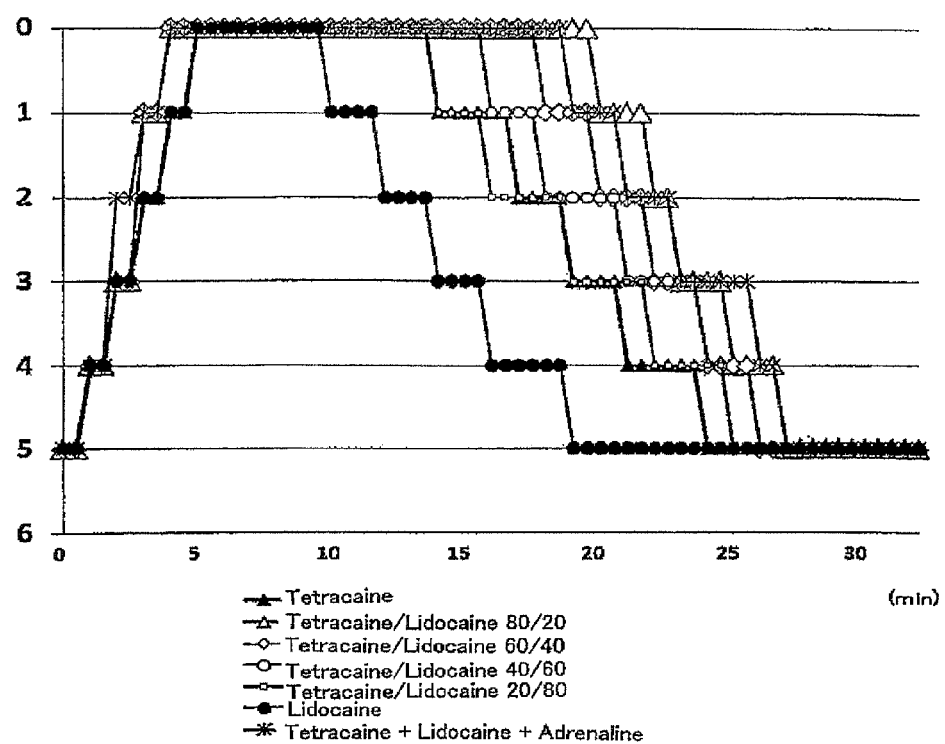
[FIG. 4] It is a graph that represents the relation of the blending ratio (mass ratio) of conventionally used lidocaine (Xylocaine) and tetracaine (COPALON), with the expression time of anesthetic effects.

Various surface anesthetic agents containing tetracaine and/or lidocaine mentioned above were applied to the buccal mucosal membrane, and then a needle was stabbed, and the time for the painless effect to be exerted and the time for the pain to start again were measured. The results thereof are shown in FIG. 4. Among the case where tetracaine was used alone (-▲-), the case where lidocaine was used alone (-●-), the case where COPALON and Xylocaine jelly were used in combination in 80:20(-△-), 60:40(-◇-), 40:60(-○-) and 20:80 (-□-) of COPALON:Xylocaine jelly, and the case where adrenaline was used in combination with tetracaine and lidocaine (-*-), it required 3 minutes or more for the painless effect to be exerted after the application. From these results, it was found that when tetracaine and lidocaine were used in combination, or when adrenaline was used in combination with tetracaine and lidocaine, the fast-acting property of the surface anesthetic action did not improve synergistically.

INDUSTRIAL APPLICABILITY

The present invention is used as a surface anesthetic agent or a pain-relieving agent in the medical fields, particularly in buccal surgery, urology department, surgery and the like.

The invention claimed is:

1. A method of treating a patient in need of anesthesia, comprising administering to a buccal mucosal membrane of said patient in need thereof a sufficient amount of a pharmaceutical composition to provide an anesthetic effect, wherein the composition comprises lidocaine and ethyl paraaminobenzoate in a mass ratio of from 6:94 to 18:82.

2. The method according to claim 1, wherein said pharmaceutical composition further comprises from 0.001 to 0.1 part by mass of adrenaline with respect to total 100 parts by mass of lidocaine and ethyl paraaminobenzoate.

3. The method according to claim 1 or 2, wherein said anesthetic effect is provided within three minutes of administration.

4. The method according to claim 3, wherein said anesthetic effect is provided within one to two minutes of administration.

* * * * *